(12) United States Patent
Lee et al.

(10) Patent No.: US 10,514,450 B2
(45) Date of Patent: Dec. 24, 2019

(54) ULTRASOUND APPARATUS AND OPERATING METHOD THEREOF

(71) Applicants: SAMSUNG MEDISON CO., LTD., Hongcheon-gun, Gangwon-do (KR); SOGANG UNIVERSITY RESEARCH FOUNDATION, Seoul (KR)

(72) Inventors: Woo-youl Lee, Gangwon-do (KR); Tae-kyong Song, Seoul (KR); Hyun-gil Kang, Daejeon (KR); Ji-won Park, Seoul (KR)

(73) Assignees: SAMSUNG MEDISON CO., LTD., Hongcheon-gun, Gangwon-do (KR); SOGANG UNIVERSITY RESEARCH FOUNDATION, Seoul (KR)

( * ) Notice: Subject to any disclaimer, the term of this patent is extended or adjusted under 35 U.S.C. 154(b) by 141 days.

(21) Appl. No.: 15/279,074

(22) Filed: Sep. 28, 2016

(65) Prior Publication Data
US 2017/0090023 A1 Mar. 30, 2017

(30) Foreign Application Priority Data
Sep. 30, 2015 (KR) ........................ 10-2015-0137624

(51) Int. Cl.
*G01S 7/52* (2006.01)
*A61B 8/00* (2006.01)
(Continued)

(52) U.S. Cl.
CPC ........ *G01S 7/52085* (2013.01); *A61B 8/4472* (2013.01); *A61B 8/4494* (2013.01);
(Continued)

(58) Field of Classification Search
None
See application file for complete search history.

(56) References Cited

U.S. PATENT DOCUMENTS 6,500,120 B1 12/2002 Anthony
6,705,995 B1 3/2004 Poland et al.
(Continued)

FOREIGN PATENT DOCUMENTS

EP 3111849 A1 1/2017
KR 10-2013-0032163 A 4/2013
(Continued)

OTHER PUBLICATIONS

Extended European Search Report dated Feb. 21, 2017 issued in European Patent Application No. 161910633.
(Continued)

*Primary Examiner* — Hovhannes Baghdasaryan
(74) *Attorney, Agent, or Firm* — Morgan, Lewis & Bockius LLP

(57) ABSTRACT

A beamformer for performing analog beamforming of ultrasound signals received from a plurality of transducer devices, the beamformer includes: first analog devices configured to output first ultrasound signals by delaying or transmitting the ultrasound signals based on a predetermined delay time; second analog devices configured to store first sub-ultrasound signals from among the first ultrasound signals, and to output the first sub-ultrasound signals depending on whether the first sub-ultrasound signals are repeatedly used; and a processor configured to control the delay time, and to perform the analog beamforming by summing the first ultrasound signals which correspond to the plurality of transducer devices and which are outputted depending on the delay time.

17 Claims, 15 Drawing Sheets

(51) Int. Cl.
    *G01S 15/89* (2006.01)
    *G10K 11/34* (2006.01)
(52) U.S. Cl.
    CPC ...... *G01S 7/52023* (2013.01); *G01S 15/8915* (2013.01); *G10K 11/346* (2013.01); *G01S 7/5208* (2013.01)

(56) References Cited

U.S. PATENT DOCUMENTS

| | | |
|---|---|---|
| 2001/0054744 A1* | 12/2001 | Scott-Thomas ...... H04N 5/2352 257/443 |
| 2005/0131299 A1 | 6/2005 | Robinson et al. |
| 2010/0063399 A1* | 3/2010 | Walker ............... G01N 29/0654 600/459 |
| 2013/0077445 A1 | 3/2013 | Um et al. |
| 2016/0363657 A1 | 12/2016 | Nakagawa et al. |

FOREIGN PATENT DOCUMENTS

| | | |
|---|---|---|
| KR | 10-1263192 B1 | 5/2013 |
| WO | 2015/128974 A1 | 9/2015 |

OTHER PUBLICATIONS

European Office Action dated Jul. 12, 2019 issued in European Patent Application No. 16191063.3.

\* cited by examiner

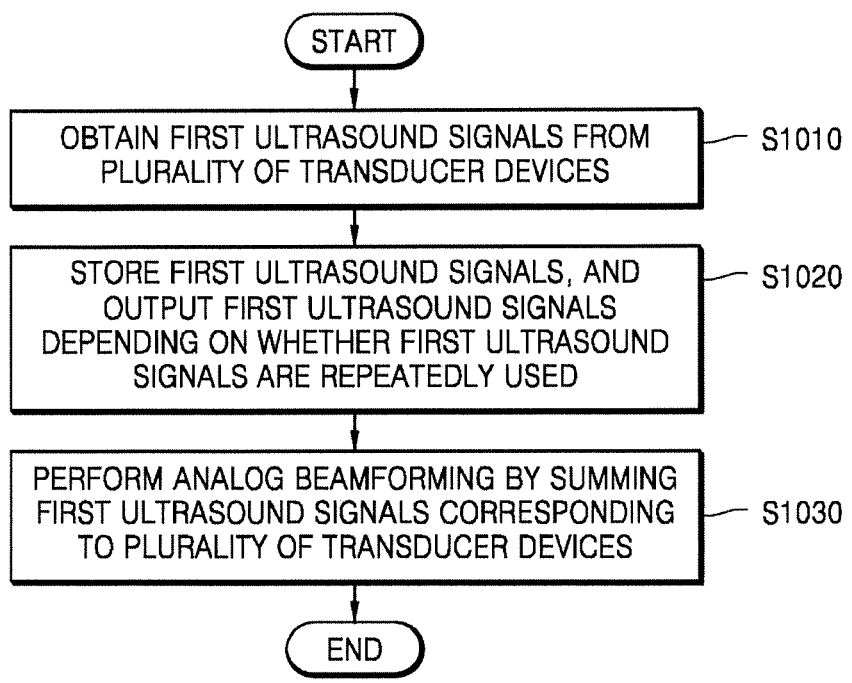

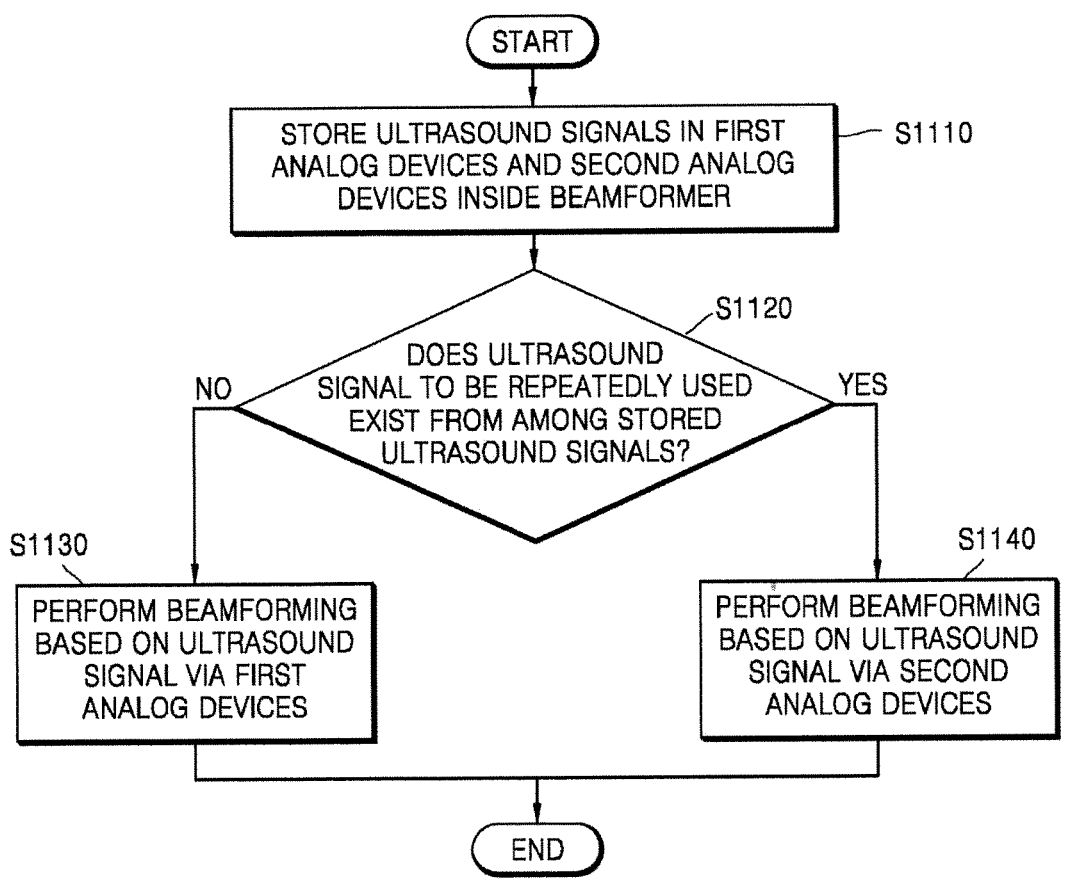

ULTRASOUND APPARATUS AND OPERATING METHOD THEREOF

CROSS-REFERENCE TO RELATED APPLICATION

This application claims the benefit of Korean Patent Application No. 10-2015-0137624, filed on Sep. 30, 2015, in the Korean Intellectual Property Office, the disclosure of which is incorporated herein in its entirety by reference.

BACKGROUND

1. Field

The present disclosure relates to ultrasound apparatuses and operating methods thereof, and more particularly, to ultrasound apparatuses for performing beamforming and methods thereof.

2. Description of the Related Art

Ultrasound diagnosis apparatuses transmit ultrasound signals generated by transducers of a probe to an object and receive echo signals reflected from the object, thereby obtaining at least one image of an internal part of the object.

In particular, ultrasound diagnosis apparatuses are used for medical purposes including observation of the interior of an object, detection of foreign substances, and diagnosis of damage to the object.

Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

SUMMARY

A beamforming method according to an embodiment may perform beamforming by using a small number of circuit devices and thus reduce a size of a system and reduce an amount of operations.

Provided are non-transitory computer-readable recording media having recorded thereon a program for executing a method of performing beamforming on a computer.

Additional aspects will be set forth in part in the description which follows and, in part, will be apparent from the description, or may be learned by practice of the presented embodiments.

According to an aspect of an embodiment, a beamformer for performing analog beamforming of ultrasound signals received from a plurality of transducer devices, the beamformer includes: first analog devices configured to output first ultrasound signals by delaying or transmitting the ultrasound signals based on a predetermined delay time; second analog devices configured to store first sub-ultrasound signals from among the first ultrasound signals, and to output the first sub-ultrasound signals depending on whether the first sub-ultrasound signals are repeatedly used; and a processor configured to control the delay time, and to perform the analog beamforming by summing the first ultrasound signals which correspond to the plurality of transducer devices and which are outputted depending on the delay time.

The second analog devices may be configured to store the first sub-ultrasound signals when the first sub-ultrasound signals from among the first ultrasound signals are output from the first analog devices, and to output the first sub-ultrasound signals when the first sub-ultrasound signals are repeatedly used in order to obtain an ultrasound image.

The second analog devices may include: a first capacitor configured to store the first sub-ultrasound signals; and a control line configured to output the first sub-ultrasound signals stored in the first capacitor.

The processor may be further configured to obtain an ultrasound signal used at least two times by applying a clock signal to the control line.

The processor may be further configured to control the first analog devices to transmit or receive each of the ultrasound signals depending on the delay time and output the first ultrasound signals.

The first analog devices may include: sample switches, one side of each of which are respectively connected to the plurality of transducer devices; sample capacitors respectively connected to the other sides of the sample switches; read-out switches one side of each of which are respectively connected to the sample capacitors, and the other sides are connected to an output terminal; the output terminal of the first ultrasound signals output from the read-out switches; and a switch controller configured to control a switching operation of the sample switches and the read-out switches.

The switch controller may include: a first shift register configured to control the sample switches; and a second shift register configured to control the read-out switches.

The beamformer may further include: a clock generator configured to generate a plurality of clock signals having different frequencies, and the first analog devices may transmit or delay each of the received ultrasound signals by the delay time based on the plurality of clock signals.

When the plurality of transducer devices complete sampling of ultrasound signals received from a relevant focusing point, the processor may be further configured to sum the first ultrasound signals which correspond to the plurality of transducer devices and which are outputted depending on the delay time by using an analog method.

The plurality of transducer devices may be arranged in a one-dimensional (1D) manner or a two-dimensional (2D) manner.

According to an aspect of another embodiment, an ultrasound imaging apparatus includes: a two-dimensional (2D) transducer array including a plurality of transducer devices arranged in a horizontal direction and a vertical direction; and an analog beamformer configured to perform analog beamforming based on ultrasound signals received from the plurality of transducer devices, and the analog beamformer includes: first analog devices configured to output first ultrasound signals by delaying or transmitting the ultrasound signals based on a predetermined delay time; second analog devices configured to store first sub-ultrasound signals, and to output the first sub-ultrasound signals depending on whether the first sub-ultrasound signals are repeatedly used; and a processor configured to perform the analog beamforming by summing the first ultrasound signals which correspond to the plurality of transducer devices and which are outputted depending on the delay time.

The apparatus may further include: a digital beamformer, and the analog beamformer may perform beamforming inside a sub-aperture that divides the transducer devices by a predetermined number, and the digital beamformer may perform beamforming between sub-apertures.

According to an aspect of another embodiment, a method of performing analog beamforming of ultrasound signals received from a plurality of transducer devices, the method includes: outputting first ultrasound signals by delaying or transmitting the ultrasound signals based on a predetermined delay time; storing first sub-ultrasound signals, and outputting the first sub-ultrasound signals depending on whether the first sub-ultrasound signals are repeatedly used; and performing the analog beamforming by summing the first ultrasound signals which correspond to the plurality of transducer devices and which are outputted depending on the delay time.

The storing of the first sub-ultrasound signals, and the outputting of the first sub-ultrasound signals depending on whether the first sub-ultrasound signals are repeatedly used may include: storing the first sub-ultrasound signals when the first sub-ultrasound signals from among the first ultrasound signals are output; and outputting the first sub-ultrasound signals when the first sub-ultrasound signals are repeatedly used in order to obtain an ultrasound image.

The method may further include: controlling first analog devices to transmit or receive each of the ultrasound signals depending on the delay time and output the first ultrasound signals.

The method may further include: generating a plurality of clock signals having different frequencies, and the outputting of the first ultrasound signals may include: transmitting or delaying each of the received ultrasound signals by the delay time based on the plurality of clock signals.

The performing of the analog beamforming may include: completing, at the plurality of transducer devices, sampling of ultrasound signals received from a relevant focusing point.

The plurality of transducer devices may be arranged in a one-dimensional (1D) manner or a 2D manner.

The method may further include: performing analog beamforming inside a sub-aperture that divides the transducer devices by a predetermined number, and performing digital beamforming between sub-apertures.

According to an aspect of another embodiment, a non-transitory computer-readable recording medium having recorded thereon a program for executing a method of performing analog beamforming of ultrasound signals received from a plurality of transducer devices is provided, and the method include: outputting first ultrasound signals by delaying or transmitting the ultrasound signals based on a predetermined delay time; storing first sub-ultrasound signals, and outputting the first sub-ultrasound signals depending on whether the first sub-ultrasound signals are repeatedly used; and performing the analog beamforming by summing the first ultrasound signals which correspond to the plurality of transducer devices and which are outputted depending on the delay time.

BRIEF DESCRIPTION OF THE DRAWINGS

These and/or other aspects will become apparent and more readily appreciated from the following description of the embodiments, taken in conjunction with the accompanying drawings in which:

FIG. 10 is a flowchart illustrating a beamforming method according to an embodiment;

FIG. 11 is a flowchart illustrating a beamforming method according to another embodiment.

DETAILED DESCRIPTION

Figure 1:
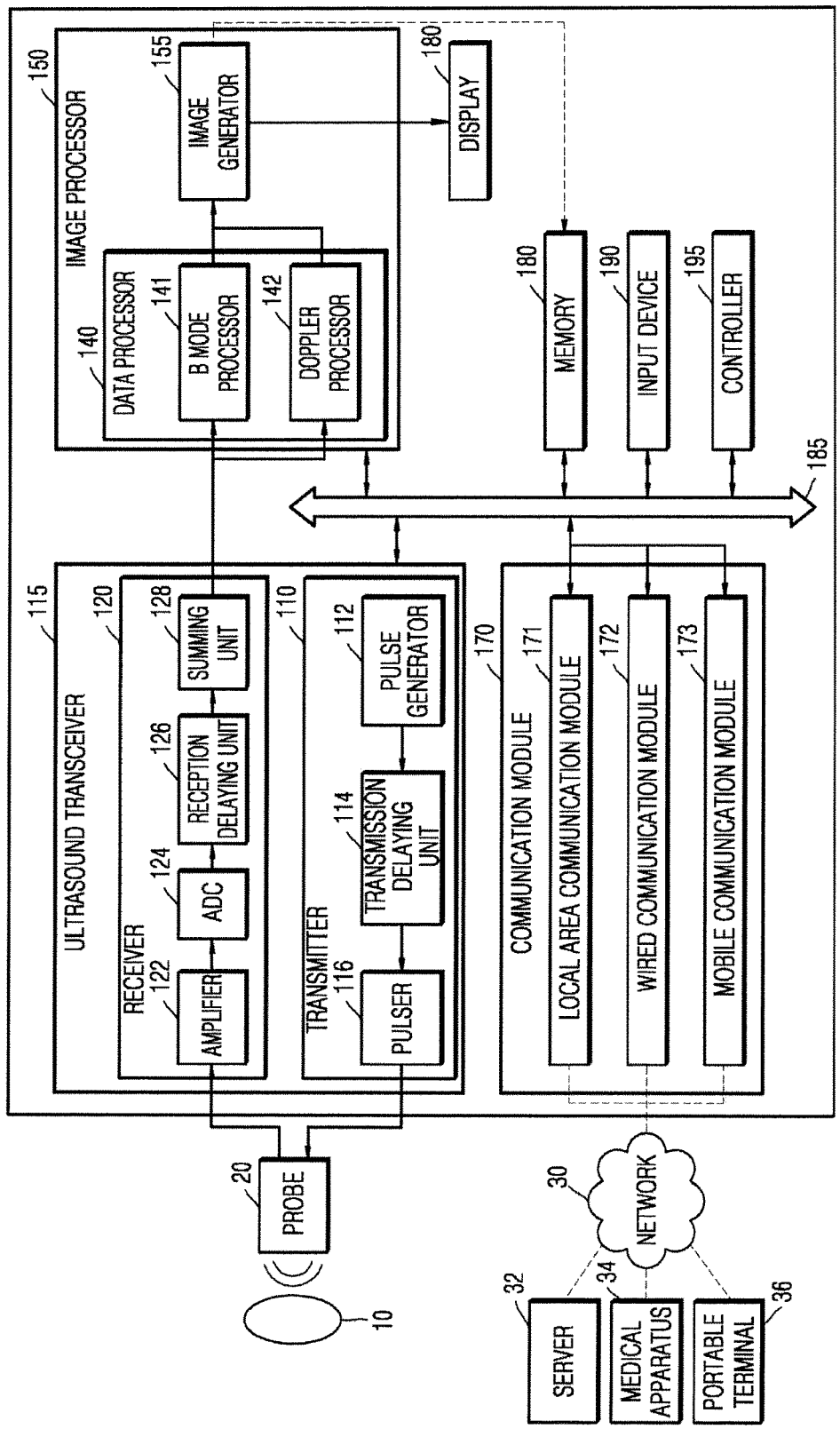
FIG. 1 is a block diagram showing a configuration of an ultrasound diagnosis apparatus according to an embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

When a part "includes" or "comprises" an element, unless there is a particular description contrary thereto, the part can further include other elements, not excluding the other elements. Also, the term "unit" in the specification means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with a smaller number of components and "units", or may be divided into additional components and "units".

While such terms as "first," "second," etc., may be used to describe various components, such components are not limited thereto. These terms are used only to distinguish one component from another. For example, a first component may be referred to as a second component without departing from the scope of the inventive concept, and similarly, a second component may be referred to as a first component. As used herein, the term "and/or" includes any and all combinations of one or more of the associated listed items. Expressions such as "at least one of," when preceding a list of elements, modify the entire list of elements and do not modify the individual elements of the list.

In the present specification, an "image" may refer to multi-dimensional data composed of discrete image elements (e.g., pixels in a two-dimensional (2D) image and voxels in a three-dimensional (3D) image).

Throughout the specification, an "ultrasound image" refers to an image of an object, which is obtained using ultrasound waves. An ultrasound image may denote an image obtained by irradiating an ultrasound signal generated from a transducer of a probe to an object, and receiving information of an echo signal reflected by the object. Also, the ultrasound image may be variously implemented, and for example, the ultrasound image may be at least one of an amplitude (A) mode image, a brightness (B) mode image, a color (C) mode image, and a Doppler (D) mode image. Also, the ultrasound image may be a two-dimensional (2D) image or a three-dimensional (3D) image.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

FIG. 1 is a block diagram showing a configuration of an ultrasound diagnosis apparatus 100 according to an embodiment.

Referring to FIG. 1, the ultrasound diagnosis apparatus 100 may include a probe 20, an ultrasound transceiver 115, an image processor 150, a display 160, a communication module 170, a memory 180, a user input unit 190, and a controller 195. Also, the above-mentioned components may be connected with each other via a bus 185, and the image processor 150 may include an image generator 155, a cross-section information detector 130, and a display 160.

A person of ordinary skill in the art will understand that other general purpose components besides the components illustrated in FIG. 1 may be further included.

In some embodiments, the ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly, and according to embodiments, the ultrasound diagnosis apparatus 100 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 124 by delay times necessary for determining reception directionality, and the summing unit 128 generates ultrasound data by summing the echo signals processed by the reception delaying unit 126.

The image processor 150 generates an ultrasound image by scan-converting ultrasound data generated by the ultrasound transceiver 115.

The ultrasound image may be not only a grayscale ultrasound image obtained by scanning an object in an amplitude (A) mode, a brightness (B) mode, and a motion (M) mode, but also may represent motion of an object by using a Doppler image. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 141 extracts B mode components from ultrasound data and processes the B mode components. An image generator 155 may generate an ultrasound image indicating signal intensities as brightness based on the extracted B mode components 141.

Similarly, a Doppler processor 142 may extract Doppler components from ultrasound data, and the image generator 155 may generate a Doppler image indicating a movement of an object as colors or waveforms based on the extracted Doppler components.

The image generator 155 may generate a 2D ultrasound image or a 3D ultrasound image of an object, and may also generate an elastic image that shows a degree of deformation of an object 10 depending on pressure. Furthermore, the image generator 155 may display various pieces of additional information in an ultrasound image by using text and graphics. In addition, the generated ultrasound image may be stored in the memory 180.

A display 160 displays the generated ultrasound image. The display 160 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 160 according to embodiments.

The display 160 may include at least one of a liquid crystal display (LCD), a thin film transistor-liquid crystal display (TFT-LCD), an organic light-emitting diode (OLED), a flexible display, a 3D display, and an electrophoretic display.

Also, in the case where the display 160 and a user input unit configure a touchscreen by forming a layered structure, the display 160 may be used as not only an output unit but also an input unit that may receive information via a user's touch.

The touchscreen may be configured to detect even a touch pressure as well as a touch location and a touched area. Also, the touchscreen may be configured to detect not only a real-touch but also a proximity touch.

In the specification, a "real-touch" denotes a case where a pointer is actually touched onto a screen, and a "proximity-touch" denotes a case where a pointer does not actually touch a screen but is held apart from a screen by a predetermined distance. In the specification, a pointer denotes a touch tool for touching or proximity-touching a specific portion of a displayed screen. For example, a pointer may be an electronic pen, a finger, etc.

Although not shown in the drawings, the ultrasound diagnosis apparatus 100 may include various sensors inside or in the vicinity of a touchscreen in order to detect a direct touch or a proximity touch with respect to the touchscreen. An example of a sensor for detecting a touch with respect to the touchscreen includes a tactile sensor.

The tactile sensor denotes a sensor for detecting a contact of a specific object to a degree felt by a person or more. The tactile sensor may detect various information such as roughness of a contact surface, hardness of a contact object, and the temperature of a contact point.

Also, an example of a sensor for detecting a touch with respect to the touchscreen includes a proximity sensor. The proximity sensor denotes a sensor for detecting an object approaching a predetermined detection surface or the existence of an object in the neighborhood by using an electromagnetic force or an infrared ray without any mechanical contact.

An example of a proximity sensor includes a transmissive photoelectric sensor, a direct reflective photoelectric sensor, a mirror reflective photoelectric sensor, a high frequency oscillation type proximity sensor, a capacitive proximity sensor, a magnetic proximity sensor, an infrared proximity sensor, etc.

The communication module 170 is connected to a network 30 by wire or wirelessly to communicate with an external device or a server. The communication module 170 may exchange data with a hospital server or another medical apparatus in a hospital, which is connected thereto via a PACS. Furthermore, the communication module 170 may perform data communication according to the digital imaging and communications in medicine (DICOM) standard.

The communication module 170 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 170 may receive information about a diagnosis history or medical treatment schedule of a patient from a server and utilizes the received information to diagnose the patient. Furthermore, the communication module 170 may perform data communication not only with a server or a medical apparatus in a hospital, but also with a portable terminal of a medical doctor or patient.

The communication module 170 is connected to the network 30 by wire or wirelessly to exchange data with a server 32, a medical apparatus 34, or a portable terminal 36.

The communication module 170 may include one or more components for communication with external devices. For example, the communication module 1300 may include a local area communication module 171, a wired communication module 172, and a mobile communication module 173.

The local area communication module 171 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 172 refers to a module for communication using electric signals or optical signals. Examples of wired communication techniques according to an embodiment may include communication via a twisted pair cable, a coaxial cable, an optical fiber cable, and an Ethernet cable.

The mobile communication module 173 transmits or receives wireless signals to or from at least one selected from a base station, an external terminal, and a server on a mobile communication network. The wireless signals may be voice call signals, video call signals, or various types of data for transmission and reception of text/multimedia messages.

The memory 180 stores various data processed by the ultrasound diagnosis apparatus 100. For example, the memory 180 may store medical data related to diagnosis of an object, such as ultrasound data and an ultrasound image that are input or output, and may also store algorithms or programs which are to be executed in the ultrasound diagnosis apparatus 100.

The memory 180 may be any of various storage media, e.g., a flash memory, a hard disk drive, EEPROM, etc. Furthermore, the ultrasound diagnosis apparatus 100 may utilize web storage or a cloud server that performs the storage function of the memory 180 online.

The user input unit 190 generates input data which a user inputs in order to control an operation of the ultrasound diagnosis apparatus 100. The user input unit 190 may include a hardware configuration such as a keypad, a mouse, a touchpad, a track ball, and a jog switch, but is not limited thereto, and may further include various configurations such as an electrocardiogram measurement module, a breathing measurement module, a voice recognition sensor, a gesture recognition sensor, a fingerprint recognition sensor, an iris recognition sensor, a depth sensor, and a distance sensor.

Particularly, the user input unit 190 may also include a touchscreen in which a touchpad and the display 160 form a layered structure.

In this case, the ultrasound diagnosis apparatus 100 according to an embodiment may display an ultrasound image of a predetermined mode and a control panel for an ultrasound image on the touchscreen. Also, the ultrasound diagnosis apparatus 100 may detect a user's touch gesture for an ultrasound image via the touchscreen.

The ultrasound diagnosis apparatus 100 according to an embodiment may physically include some buttons frequently used by a user from among buttons included in a control panel of a general ultrasound apparatus, and provide the rest of the buttons in the form of a graphical user interface (GUI) via the touchscreen.

The controller 195 may control all operations of the ultrasound diagnosis apparatus 100. In other words, the controller 195 may control operations among the probe 20, the ultrasound transceiver 100, the image processor 150, the communication module 170, the memory 180, and the user input unit 190 shown in FIG. 1.

All or some of the probe 20, the ultrasound transceiver 115, the image processor 150, the communication module 170, the memory 180, the user input unit 190, and the controller 195 may be implemented as software modules. However, embodiments of the present invention are not limited thereto, and some of the components stated above may be implemented as hardware modules. Furthermore, at least one selected from the ultrasound transceiver 115, the image processor 150, and the communication module 170 may be included in the controller 195. However, embodiments of the present invention are not limited thereto.

Figure 2:
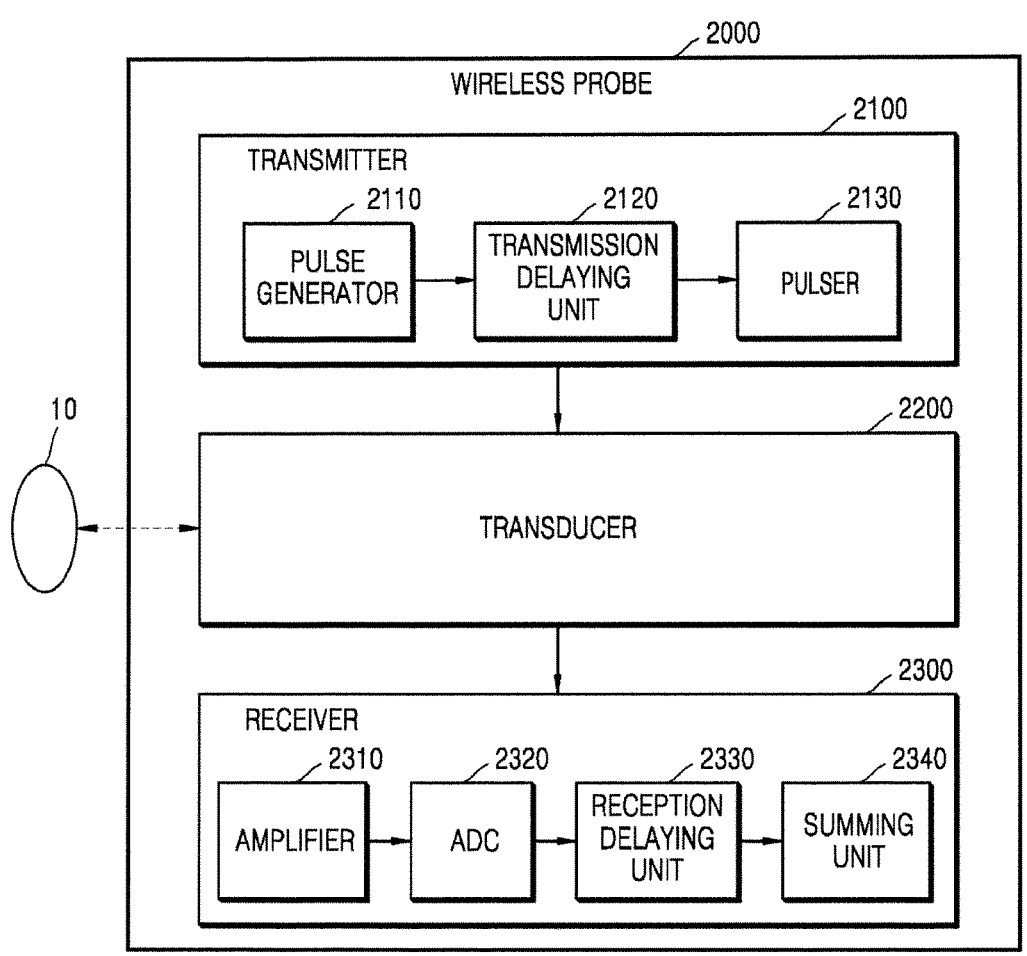
FIG. 2 is a block diagram showing a configuration of a wireless probe according to an embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

The wireless probe 2000 may be a smart apparatus that may perform ultrasound scanning by including a transducer array. Specifically, the wireless probe 2000 is a smart apparatus, scans an object by using a transducer array, and obtains ultrasound data. Then, the wireless probe 2000 may generate and/or display an ultrasound image by using the obtained ultrasound data. The wireless probe 2000 may include a display, and display a screen including a user interface screen for controlling at least one ultrasound image and/or a scan operation of an object via the display.

While a user scans a patient's predetermined body portion, which is an object, by using the wireless probe 2000, the wireless probe 2000 and the ultrasound diagnosis apparatus 100 may continue to transmit/receive predetermined data via a wireless network. Specifically, while a user scans a patient's predetermined body portion, which is an object, by using the wireless probe 2000, the wireless probe 2000 may transmit ultrasound data to the ultrasound diagnosis apparatus 100 in real-time via the wireless network. The ultrasound data may be updated in real-time and transmitted from the wireless probe 2000 to the ultrasound diagnosis apparatus 100 as ultrasound scanning is performed continuously.

Figure 3:
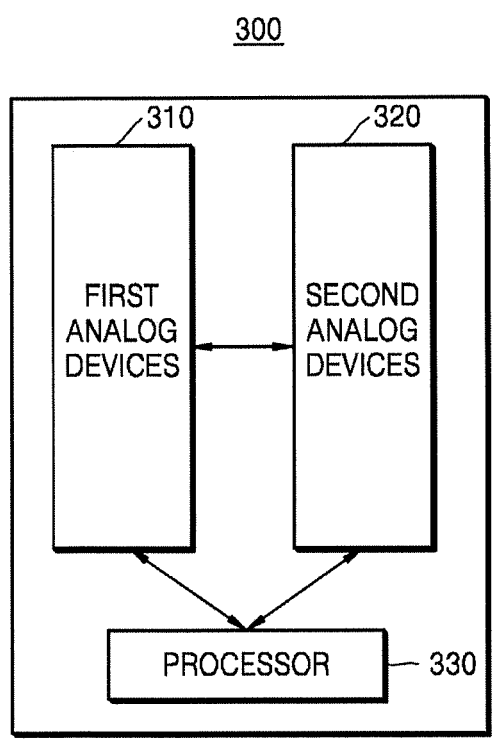
FIG. 3 is a block diagram illustrating a beamformer according to an embodiment.

FIG. 3 is a block diagram illustrating a configuration of a beamformer 300 according to an embodiment.

Throughout the specification, beamforming denotes strengthening the intensity of ultrasound signals by overlapping the ultrasound signals when transmitting/receiving the ultrasound signals by using a plurality of transducer devices. Also, one point at which a user desires to obtain ultrasound image information is referred to as a focusing point. The beamforming may be classified into analog beamforming and digital beamforming. The beamformer 300 of FIG. 3 is related to analog beamforming.

According to an embodiment, the beamformer 300 may perform analog beamforming of ultrasound signals received from the plurality of transducer devices. The beamformer 300 may delay or transmit ultrasound signals by using a circuit device. The beamformer 300 may include first analog devices 310, second analog devices 320, and a processor 330. However, all the illustrated components are not essential components. The beamformer 300 may be implemented by a greater number of components than the illustrated components, and may be implemented by a smaller number of components than the illustrated components. The above components are described below.

The first analog devices 310 may output first ultrasound signals by delaying or transmitting ultrasound signals received from a plurality of transducer devices based on a predetermined delay time. Here, the plurality of transducer devices may be arranged in one dimension or two dimensions. Also, an ultrasound signal may denote an echo signal generated by scanning an ultrasound signal.

Specifically, the first analog devices 310 may include an output terminal, sample switches, sample capacitors, read-out switches, and a switch controller. The switch controller may include a first shift register controlling the sample switches, and a second shift register controlling the read-out switches. Specific content of the first analog devices 310 is described with reference to FIG. 6.

Figure 4:
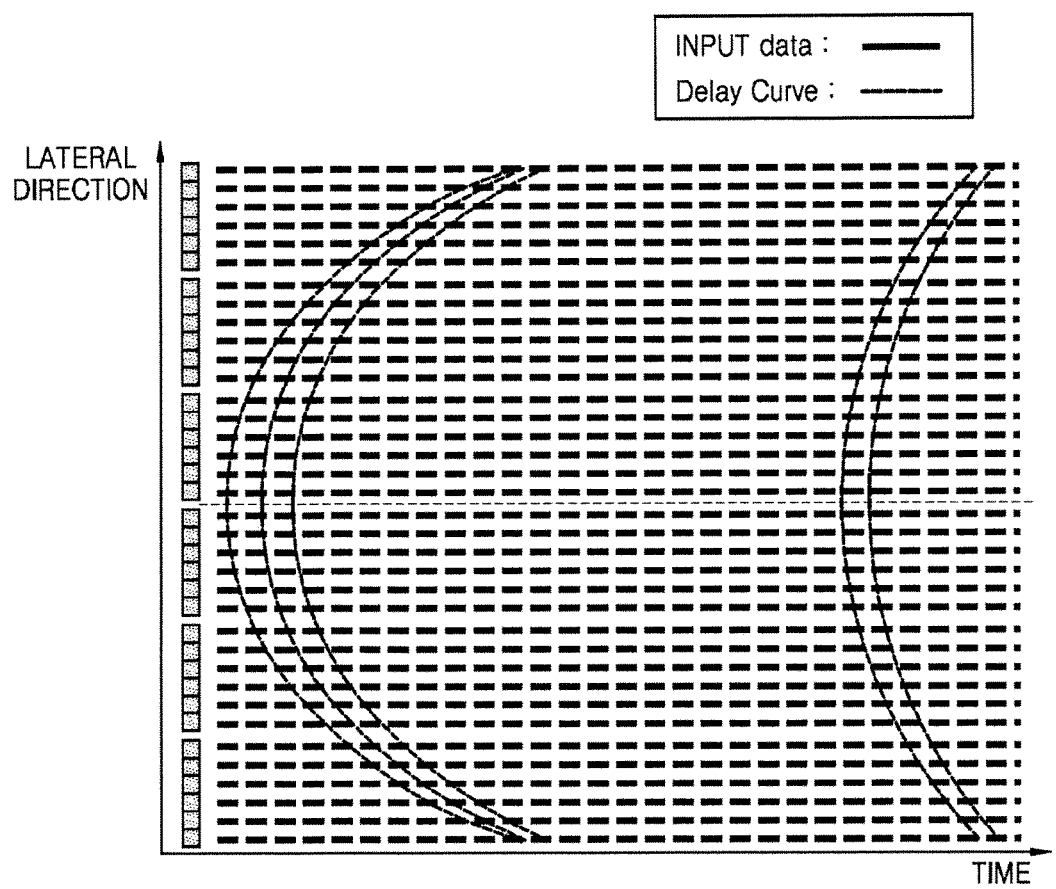
FIG. 4 is a diagram for explaining a case where an ultrasound signal should be repeatedly used, according to an embodiment.

Referring to FIG. 4, input data (for example, an ultrasound signal received from transducer devices) is a reception signal stored in a sample capacitor, and a delay curve represents a focusing delay profile that should be applied to implement different image points. As illustrated in FIG. 4, for reception dynamic beam focusing, a case of having to repeatedly use the same input data occurs.

Figure 5:
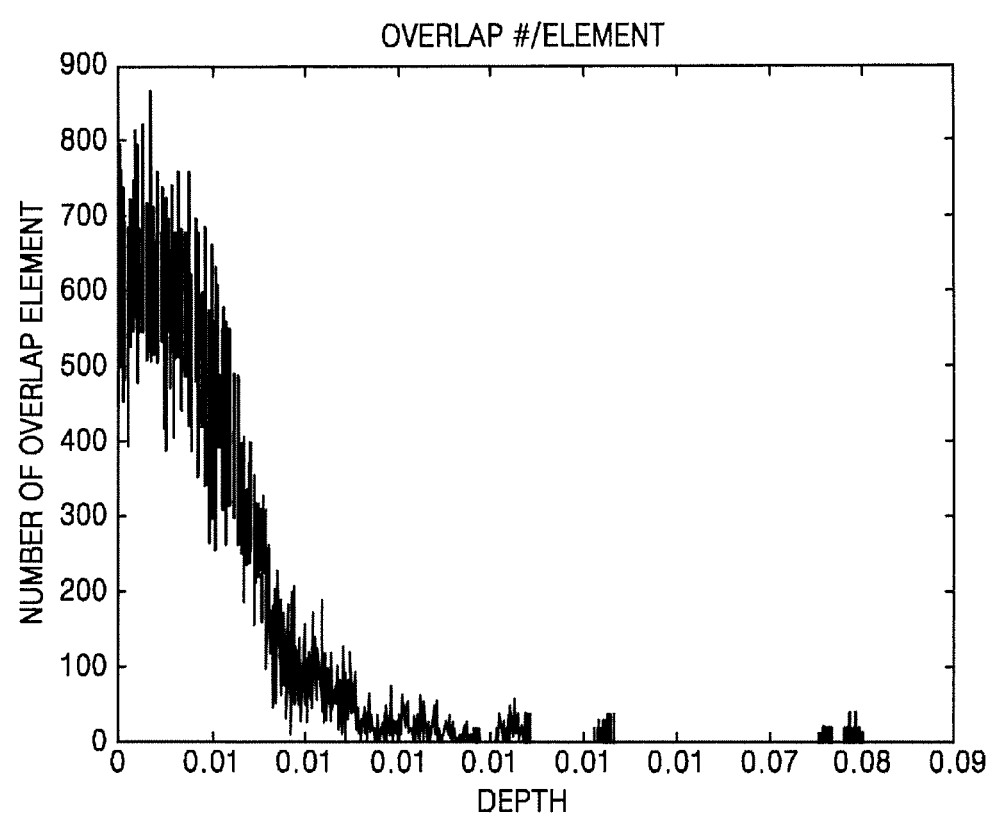
FIG. 5 is a graph illustrating a number of focusing points depending on depth according to an embodiment.

Specifically, FIG. 5 illustrates an example of a graph representing a number of focusing points depending on a depth. Referring to the graph, it is revealed that a number of focusing points that use a signal two times or more increases as a depth is small.

In the case where the first analog devices 310 repeatedly obtain an ultrasound signal to be repeatedly used from among first ultrasound signals, in view of a characteristic of a sample capacitor used as an analog RAM, a charged electron is discharged after data (a stored ultrasound signal) is read-out once, so that the data cannot be read.

The beamformer 300 may perform focusing at all image points without an error by using the first analog devices 310 and the second analog devices 320. In the case where first sub-ultrasound signals from among the first ultrasound signals are output from the first analog devices 310, the second analog devices 320 may store the first sub-ultrasound signals, and output the first sub-ultrasound signals depending on whether the first sub-ultrasound signals are repeatedly used. That is, an ultrasound signal to be repeatedly used from among the first ultrasound signals may be obtained via the second analog devices 320. A time and a number of times of an ultrasound signal to be repeatedly used may be determined by the specification of the probe and a sampling rate of data stored in the sample capacitor.

Specifically, the second analog devices 320 may include a first capacitor and a control line. The first capacitor may store the first sub-ultrasound signal, and the control line may control to output the first sub-ultrasound signal stored in the first capacitor. Also, the second analog devices 320 may include sampling switches of the first capacitor. Specifically, the first capacitor may store a first sub-ultrasound signal that is read-out from the first analog devices 310. Here, the first sub-ultrasound signal is one of first ultrasound signals output from the first analog devices 310.

Whenever sample capacitors under control of a shift register are read-out, a first ultrasound signal is stored in a first capacitor in which the read-out value is not under control of a shift register. Therefore, an ultrasound signal used at least two times from among first ultrasound signals may be obtained by not applying a system clock signal but by applying a clock signal to a control line. In other words, since an ultrasound signal that should be repeatedly used may be read-out from the first capacitor, the same data may be used.

Also, since a system clock signal is not applied to sample capacitors of the first analog devices 310, a data pull phenomenon or a data omission phenomenon does not occur at output final data after a time at which data should be repeatedly used. Therefore, the beamformer 300 may perform accurate analog beamforming by using an operation of the second analog devices 320.

The processor 330 may control a delay time, and perform analog beamforming by summing first ultrasound signals which correspond to a plurality of transducer devices and which are outputted depending on the delay time. The processor 330 delays an analog echo signal of each channel for a different time every channel, and then performs beamforming by summing values sampled from each channel by using an analog method at a specific common time point. The processor 330 may control to convert a beamforming-completed analog signal into a digital signal via an analog-to-digital converter.

The processor 330 may control the first analog devices 310 to output first ultrasound signals by transmitting or receiving ultrasound signals depending on a delay time.

Also, the beamformer 300 may further include a clock generator generating a plurality of clock signals having different frequencies. The first analog devices 310 may transmit or delay, by a delay time, each of ultrasound signals received based on a first clock signal from among the plurality of clock signals.

In the case where a plurality of transducer devices complete sampling of ultrasound signals received from a relevant focusing point, the processor 330 may sum the first ultrasound signals which correspond to the plurality of transducer devices and which are outputted depending on the delay time by using an analog method.

Since a number of cables connecting a probe with a main machine may be reduced when an ultrasound imaging apparatus performs analog beamforming, analog beamforming is more effective in an aspect of hardware than digital beamforming in the case of one dimensional transducer or a two dimensional transducer having a large number of channels.

The beamformer 300 may generally control operations of the first analog devices 310, the second analog devices 320, and the processor 330 by including a central operation processor. The central operation processor may be implemented by using an array of a plurality of logic gates, and may be implemented by a combination of a general purpose microprocessor and a memory storing a program executable by the microprocessor. Also, a person of ordinary skill in the art will understand that the central operation processor may be implemented by using other types of hardwares.

Hereinafter, various operations or applications performed by the beamformer 300 are described. Even though one of the first analog devices 310, the second analog devices 320, and the processor 330 is not specified, content which may be clearly understood or predicted by a person of ordinary skill in the art may be understood by general implementation, and the scope of the inventive concept is not limited by a name or a physical/logical structure of a specific component.

Figure 6:
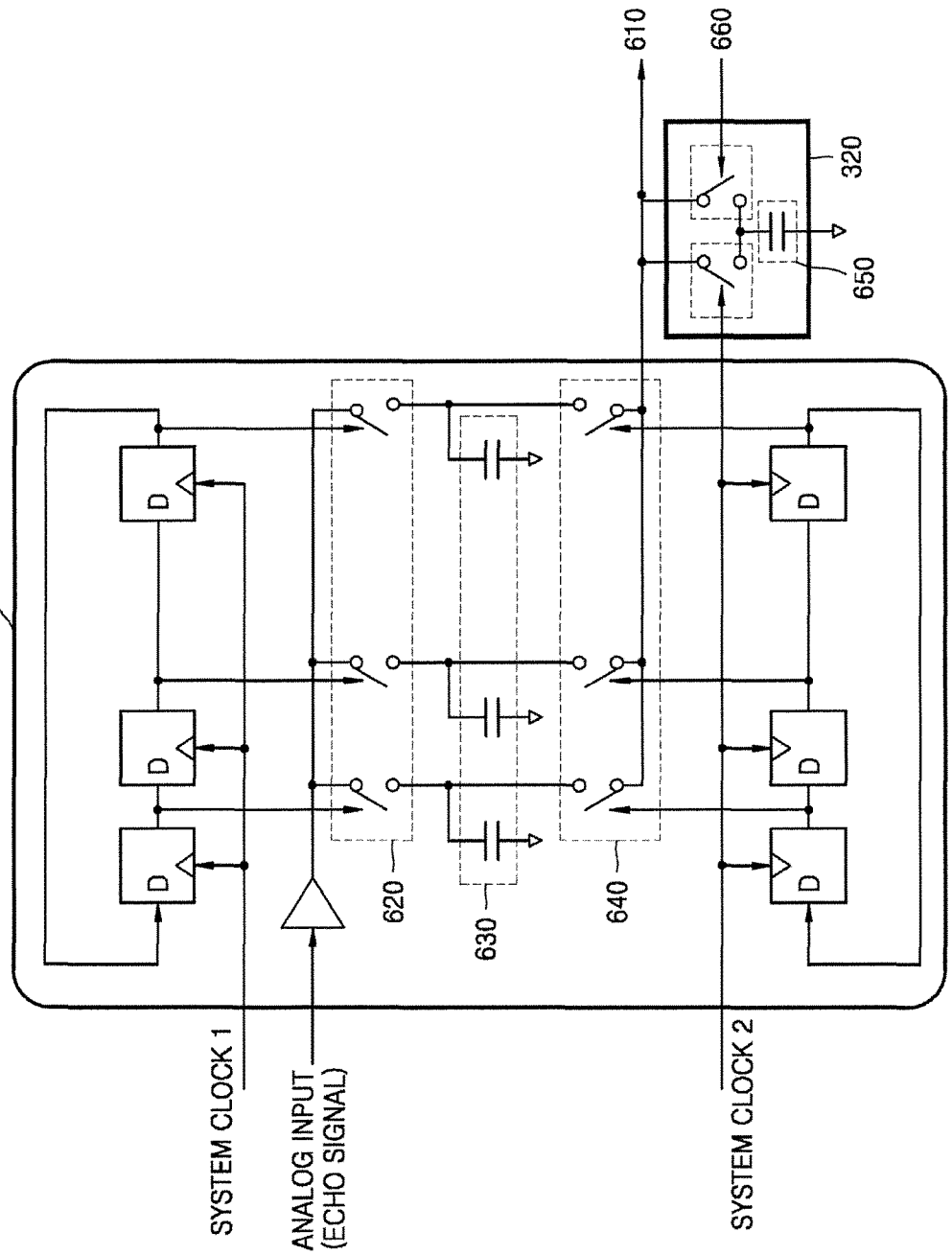
FIG. 6 is a circuit diagram illustrating a beamformer according to an embodiment.

FIG. 6 is a circuit diagram illustrating a beamformer 300 according to an embodiment.

The beamformer 300 may perform analog beamforming by using a sample/hold circuit including a capacitor. The beamformer 300 may include the first analog devices 310, the second analog devices 320, and a processor.

The first analog devices 310 may delay or transmit each of ultrasound signals based on a predetermined delay time. Specifically, the first analog devices 310 may be delay devices. The delay device may allow delay times of ultrasound signals to differ by making hold times corresponding to a difference between a sampling time and a reading time different via a plurality of sample/hold circuits.

The first analog devices 310 may include an output terminal 610, sample switches 620, sample capacitors 630, read-out switches 640, and a switch controller. The switch controller may include a first shift register controlling the sample switches 620 and a second shift register controlling the read-out switches 640.

Specifically, the output terminal 610 may sum the first ultrasound signals which correspond to the plurality of transducer devices and which are outputted depending on the delay time. One side of the sample switch may be connected with the plurality of transducer devices. One sides of the read-out switches 640 may be respectively connected with the sample capacitors 630, and the other sides of the read-out switches 640 may be connected with the output terminal 610. The switch controller may control switching operations of the sample switches 620 and the read-out switches 640.

The sample capacitors 630 samples ultrasound signals received from the plurality of transducer devices, and the first shift register controlling the sample switches 620 allows a sampling operation to be sequentially performed at each capacitor every rising edge time of a clock signal in a ring counter method. The second shift register controls the read-out switches 640 to read-out ultrasound signals stored in the sample capacitors 630.

The first shift register and the second shift register may be controlled by a system clock signal, and the second shift register may be controlled by a stall signal output from the processor of the beamformer 300.

Also, in an initial stage, which is right after power supply is connected, only one output from among a flip-flop is 1 and the rest of outputs are set to 0. When a system clock signal is applied, a location of an output 1 moves from a left flip-flop to a right flip-flop every rising edge time of the clock signal, so that sampling and read-out operations may be performed at the sample capacitors 630.

The second analog devices 320 may include a first capacitor 650 and a control line 660. The first capacitor 650 may store the first sub-ultrasound signal, and the first sub-ultrasound signal is one of first ultrasound signals output from the first analog devices. The control line 660 may control to output an ultrasound signal that is used at least two times from among first sub-ultrasound signals stored in the first capacitor 650.

FIG. 6 illustrates lots of specific matters such as component devices of a specific circuit, which are merely provided for overall understanding of the inventive concept. It is obvious to a person of ordinary skill in the art that the inventive concept may be embodied even without the specific matters. Also, a person of ordinary skill in the art will understand that other general purpose components may be further included besides the components illustrated in FIG. 6.

Figure 7A:
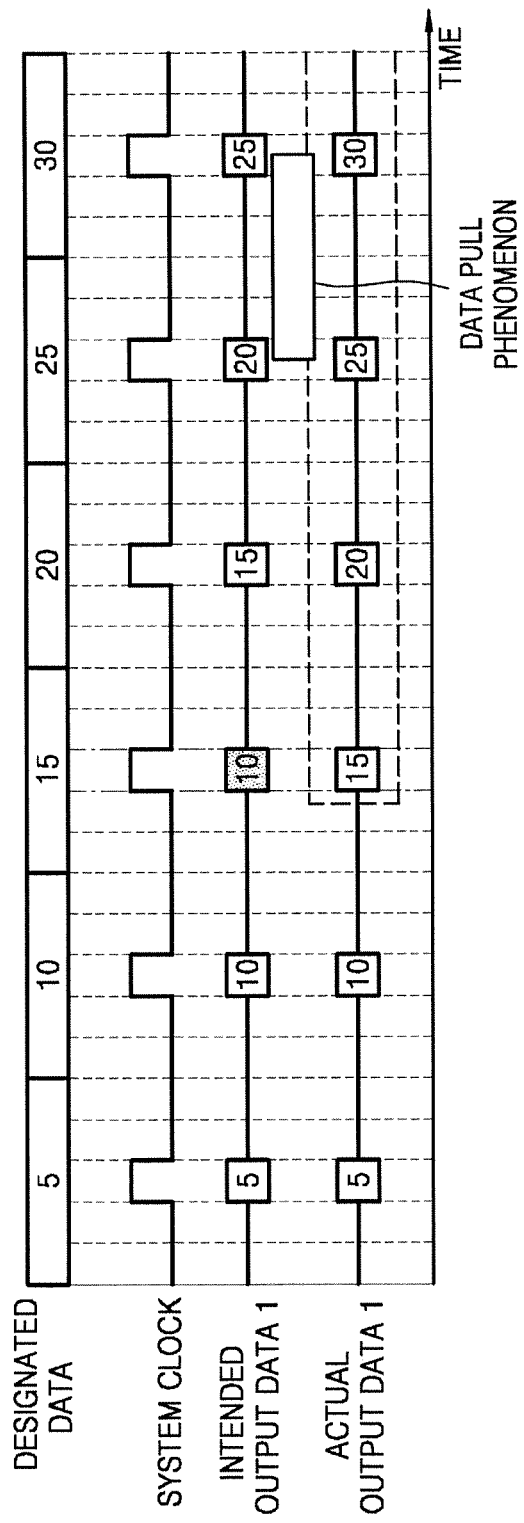
FIG. 7A is a diagram for explaining about an occurrence of an error in output data in a case where second analog devices of a beamformer are absent according to an embodiment.
Figure 7B:
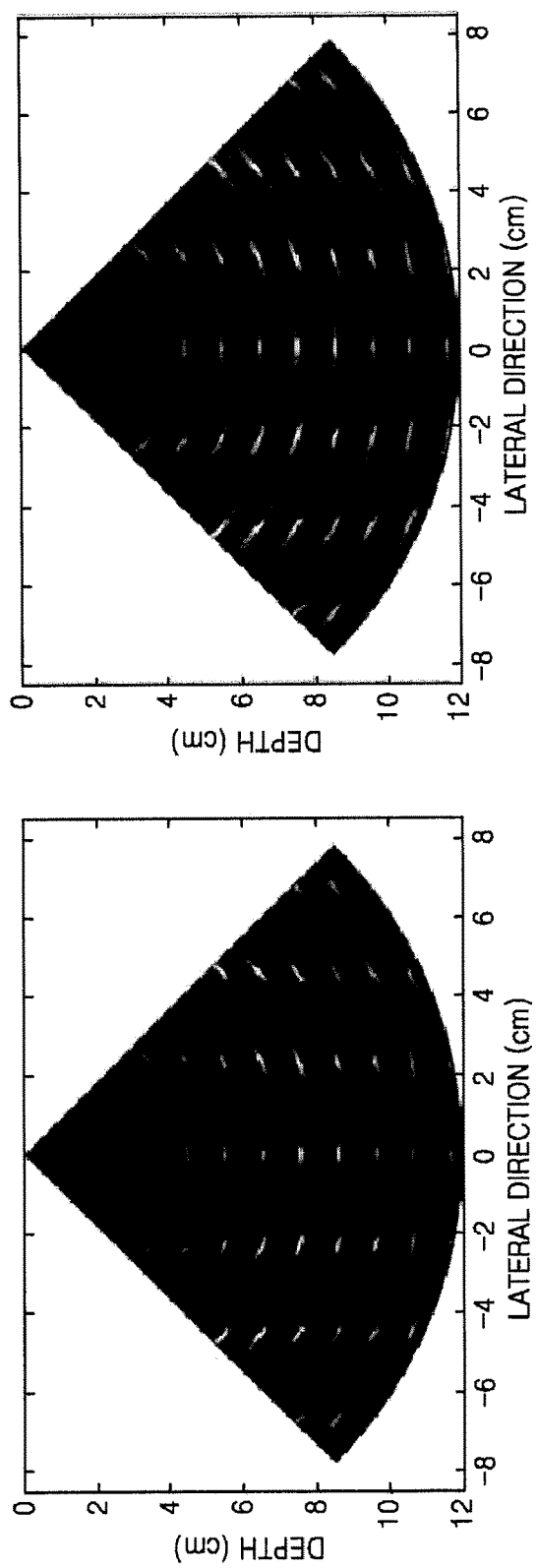
FIG. 7B is a diagram illustrating a B mode image corresponding to FIG. 7A.

FIG. 7A is a diagram for explaining occurrence of an error in output data in the case where second analog devices of a beamformer are absent according to an embodiment, and FIG. 7B is a diagram illustrating a B mode image according to disclosure of FIG. 7A.

In view of a characteristic of a capacitor used as an analog RAM in an analog beamformer of an ultrasound transducer, a charged electron is discharged after an ultrasound signal stored in the capacitor is read, so that the stored ultrasound signal cannot be read.

To obtain an ultrasound image of high image quality, for performing a reception dynamic beam focusing method that performs dynamic focusing on all image points on a scanning line, a case of having to repeatedly use the same echo signal occurs.

Referring to FIG. 7A, when a clock signal is applied in order to use the same data value after an echo signal stored in sample capacitors is read-out, since a signal to be focused with respect to the next image point is read-out, an error continues to occur in a direction in which an ultrasound wave progresses.

Specifically, in the case where a clock signal is applied in order to repeatedly use an ultrasound signal (an echo signal) stored in a sample capacitor, since the sample capacitor is controlled by a shift register, when a clock signal is applied, a value stored in the next capacitor is read-out. Therefore, a data pull phenomenon occurs from a point at which repeated use is desired. That is, an error occurs due to the data pull phenomenon. FIG. 7B is a diagram illustrating a B mode image according to disclosure of FIG. 7A. A point target is not accurately located due to the data pull phenomenon.

Figure 8A:
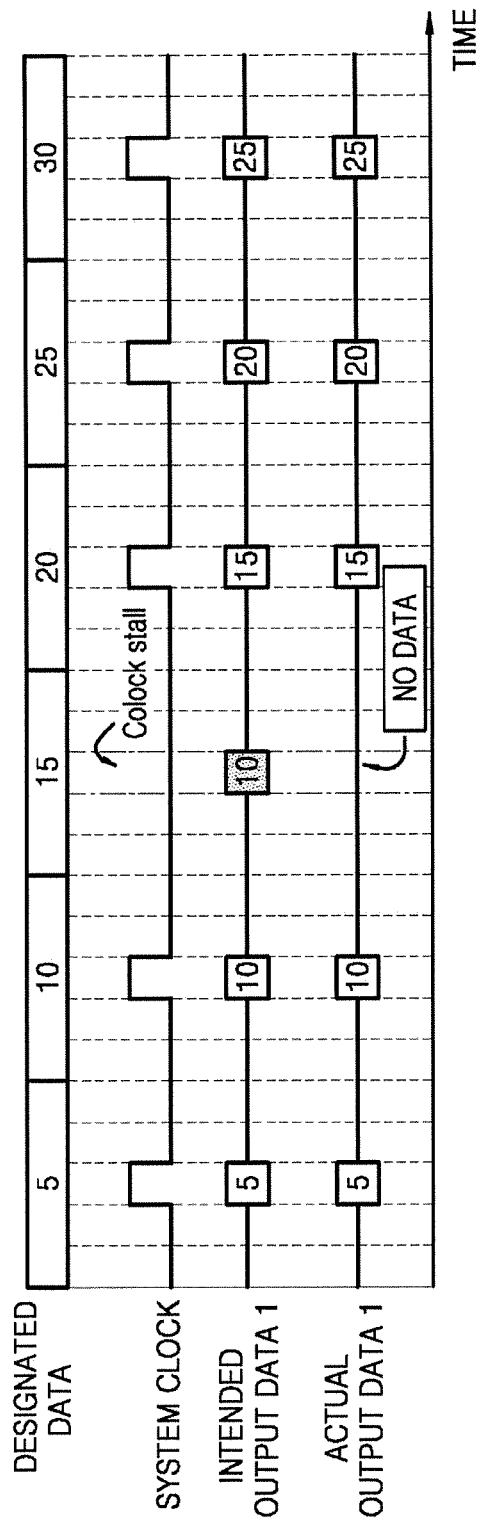
FIG. 8A is a diagram for explaining about an occurrence of an error in output data in a case where second analog devices of a beamformer are absent, according to another embodiment.
Figure 8B:
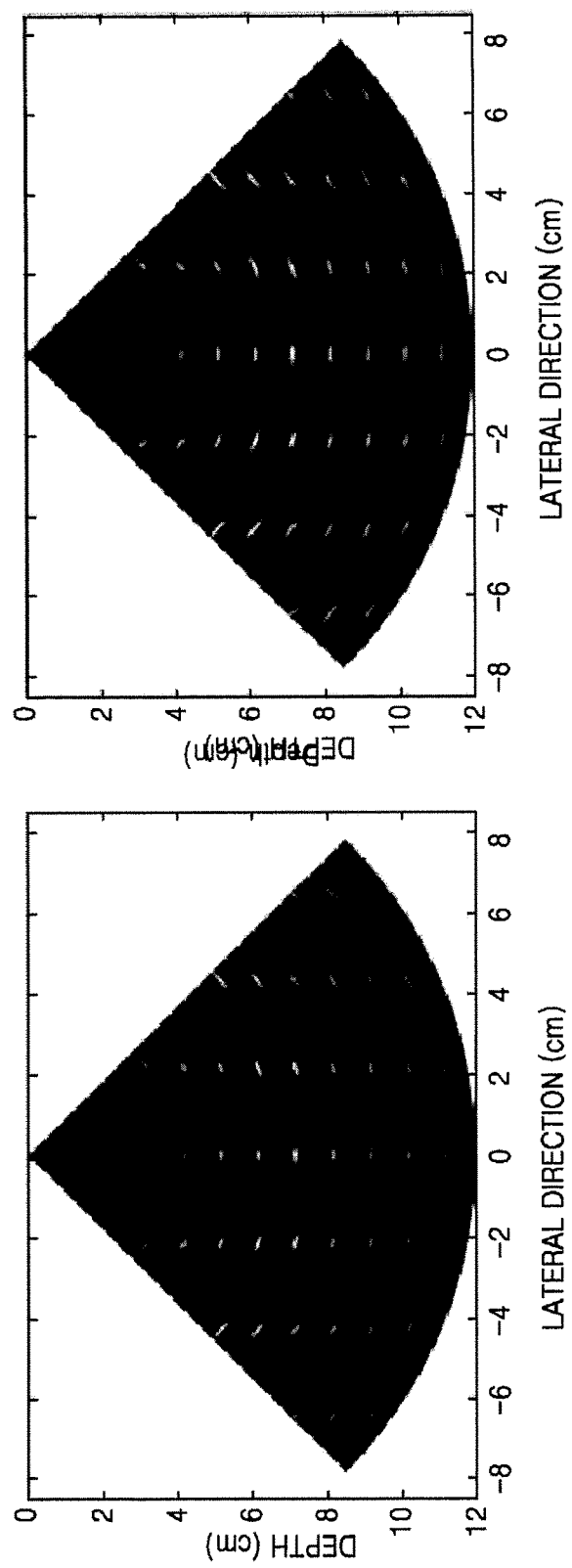
FIG. 8B is a diagram illustrating a B mode image corresponding to FIG. 8A.

FIG. 8A is a diagram for explaining occurrence of an error in output data in the case where second analog devices of a beamformer are absent according to another embodiment. FIG. 8B is a diagram illustrating a B mode image according to disclosure of FIG. 8A.

Referring to FIG. 8A, since a read-out value of a current channel is absent, an error occurs in focusing a current image point. Specifically, in the case where a clock signal is not applied in order to repeatedly use an ultrasound signal stored in a sample capacitor, the data pull phenomenon that occurs as in FIG. 7A may be avoided. However, since an ultrasound signal is absent at a point at which an ultrasound should be repeatedly used, accurate beamforming is impossible. Meanwhile, in the case of FIG. 8A, since the data pull phenomenon illustrated in FIG. 7A does not occur, a beamforming error is small compared with FIG. 7A.

As illustrated in FIG. 8B, since data is absent at a point that requires repeated use, a location of a point target is not shown accurately or the point target is not located at a near depth that requires repeated use much.

Figure 9A:
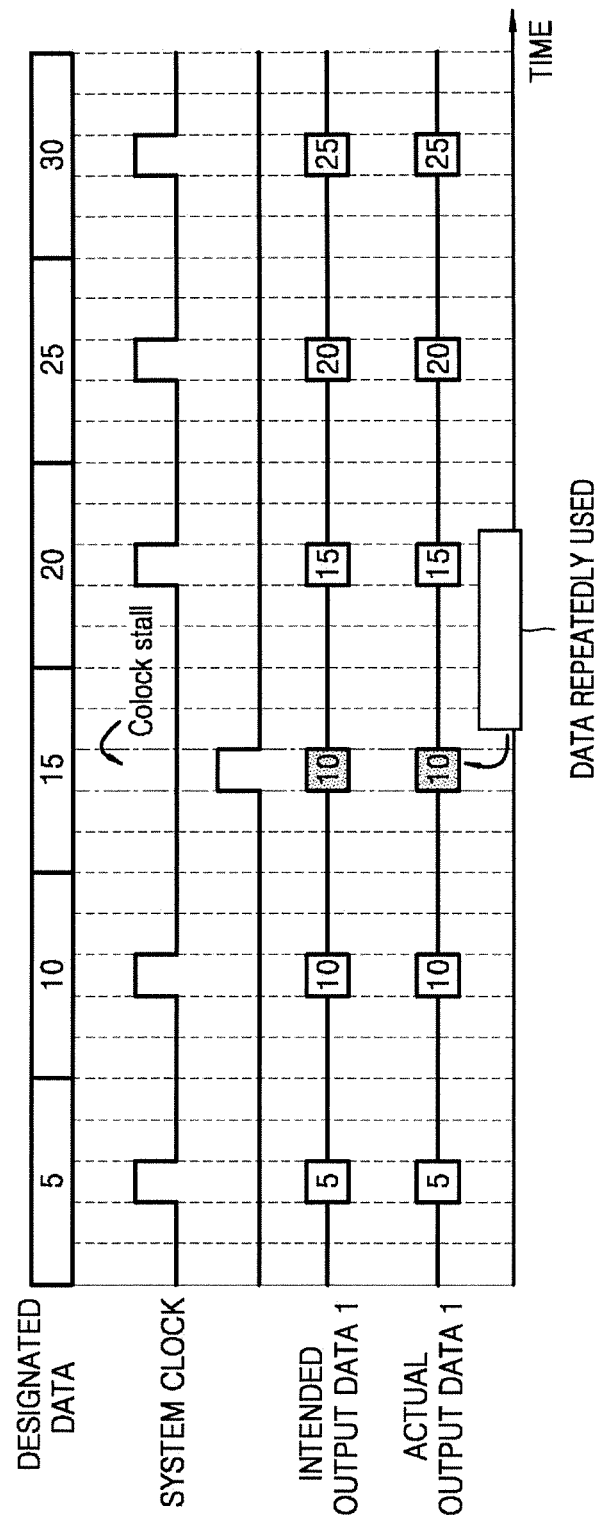
FIG. 9A is diagram illustrating that data is output without an error in a case where second analog devices of a beamformer are present.
Figure 9B:
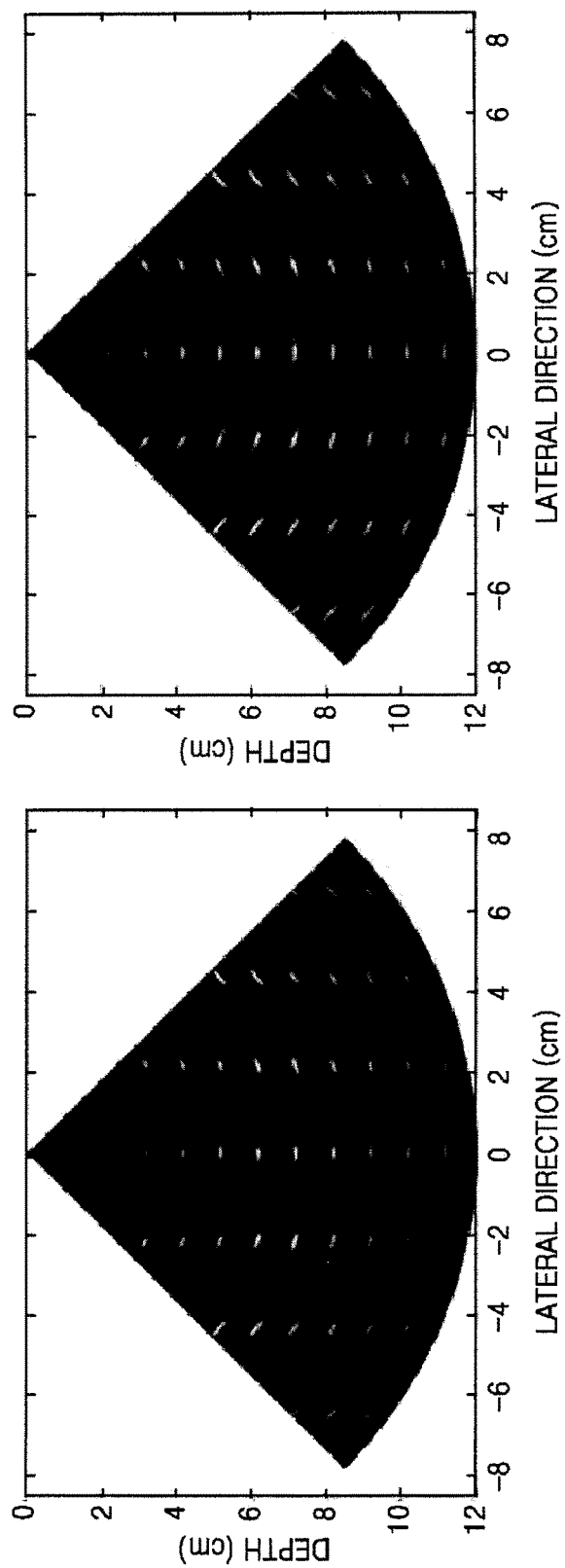
FIG. 9B is a diagram illustrating a B mode image corresponding to FIG. 9A.

FIG. 9A is diagram for explaining that data is output without an error in the case where second analog devices of a beamformer are present. FIG. 9B is a diagram illustrating a B mode image according to disclosure of FIG. 9A.

The beamformer may repeatedly use sampled ultrasound signals by adding one capacitor every channel, and remove a focusing delay error generated because repeated use is impossible.

The second analog devices may include a first capacitor storing the first sub-ultrasound signals and a control line controlling to output an ultrasound signal used at least two times from among the first sub-ultrasound signals stored in the first capacitor. Also, the second analog device may further include a sample switch that equally uses a clock signal applied to the second shift register.

Since ultrasound signals sampled at the beamformer are stored two times, all the ultrasound signals may be repeatedly used. Specifically, in regard to a repeatedly used ultrasound signal, for a first use, an ultrasound signal stored in a sample capacitor is read-out and used by applying a clock signal to the second shift register. In this case, since a sampling switch of the first capacitor is the same as a clock signal provided to the second shift register, an ultrasound signal read-out from the sample capacitor is stored in the first capacitor. After that, for a second use, the same ultrasound signal as the ultrasound signal used first may be read-out from the first capacitor by not applying a clock signal to the second shift register but applying a clock signal to the control line that reads-out the first capacitor. In the case where a repeatedly used ultrasound signal is absent, beamforming may be performed by not applying a clock signal to the control line.

It may be determined that the B mode image illustrated in FIG. 9B improves compared with the B mode image illustrated in FIGS. 7B and 8B in its quality of the ultrasound image. Specifically, quality of an image may improve at a near depth that requires a repeated use of an ultrasound signal.

FIG. 10 is a flowchart illustrating a beamforming method according to an embodiment.

Referring to FIG. 10, in operation S1010, a beamformer may output first ultrasound signals by delaying or transmitting ultrasound signals received from a plurality of transducer devices based on a predetermined delay time.

In operation S1020, the beamformer may store the first sub-ultrasound signals, and output the first sub-ultrasound signals one time depending on whether the first sub-ultrasound signals are repeatedly used. Here, in the case where the first sub-ultrasound signal from among the first ultrasound signals is output, the beamformer may store the first sub-ultrasound signal. Also, to obtain an ultrasound image, the beamformer may output a first sub-ultrasound signal in the case where first sub-ultrasound signals are repeatedly used.

In operation S1030, the beamformer may perform analog beamforming by summing first ultrasound signals which correspond to a plurality of transducer devices and which are outputted depending on the delay time.

FIG. 11 is a flowchart illustrating a beamforming method according to another embodiment.

Referring to FIG. 11, in operation S1110, the beamformer may store ultrasound signals received from a plurality of transducer devices in the first analog devices and the second analog devices inside the beamformer. The second analog devices store a first sub-ultrasound signal whenever the first sub-ultrasound signal from among first ultrasound signals is read-out from the first analog devices.

Here, the first analog devices and the second analog devices may include a sample/hold circuit that uses a capacitor in order to store ultrasound signals. Sample capacitors included in the first analog devices may be controlled by a shift register. In contrast, a capacitor included in the second analog devices is not controlled by a shift register.

In operation S1120, the beamformer may determine whether an ultrasound signal to be repeatedly used exists from among ultrasound signals stored in the first and second analog devices. When an ultrasound signal to be repeatedly used does not exist, the beamformer operates according to operation S1130. Also, when an ultrasound signal to be repeatedly used exists, the beamformer operates according to operation S1140.

In operation S1130, the beamformer may adjust a difference between a sampling time and a read-out time of stored ultrasound signals via a time difference of a clock signal provided to the first shift register and the second shift register. The beamformer may allow a signal delay time of each channel to differ and thus perform beamforming. Each shift register of the beamformer may sequentially switch the next capacitor every rising edge time of a clock signal in a ring counter method. In this case, a sample switch of each sample capacitor is controlled by the first shift register, and a read-out switch is controlled by the second shift register. To use an ultrasound signal, the beamformer may read-out and use a signal stored in a sample capacitor by applying a clock signal to the second shift register.

In operation S1140, to repeatedly use an ultrasound signal, the beamformer may read-out an ultrasound signal to be repeatedly used by applying a clock signal to a control line that reads-out a capacitor included in the second analog device without applying a clock signal to the second shift register.

Figure 12:
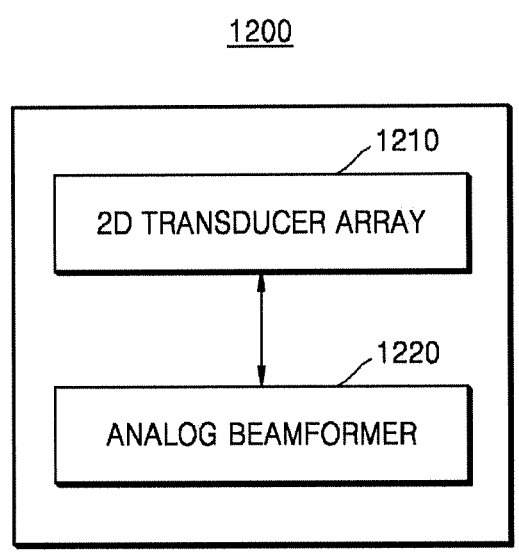
FIG. 12 is a block diagram illustrating a configuration of an ultrasound imaging apparatus according to an embodiment.

FIG. 12 is a block diagram illustrating a configuration of an ultrasound imaging apparatus 1200 according to an embodiment.

The ultrasound imaging apparatus 1200 may include a 2D transducer array 1210 and an analog beamformer 1220. However, all the illustrated components are not essential components. The ultrasound imaging apparatus 1200 may be implemented by using a greater number of components than the illustrated components, and implemented by using a less number of components than the illustrated components. Hereinafter, the components are described.

The 2D transducer array 1210 may include a plurality of transducer devices arranged in a horizontal direction and a vertical direction. The analog beamformer 1220 may perform analog beamforming based on ultrasound signals received from the plurality of transducer devices.

The analog beamformer 1220 equally corresponds to the beamformer described with reference to FIGS. 3 to 11, and repeated descriptions are omitted.

Meanwhile, the ultrasound imaging apparatus 1200 may further include a digital beamformer. The ultrasound imaging apparatus 1200 may perform analog beamforming inside a sub-aperture that divides the transducer devices by a predetermined number, and perform digital beamforming between sub-apertures. According to an embodiment, the analog beamformer 1220 may perform analog beamforming in one of a horizontal direction and a vertical direction, and the digital beamformer may perform digital beamforming in the other direction.

The ultrasound imaging apparatus 1200 may generally control the 2D transducer array 1210, the analog beamformer 1220, and the digital beamformer by including a central operation processor. The central operation processor may include an array of a plurality of logic gates, and include a combination of a general purpose microprocessor and a memory storing a program executable by the microprocessor. Also, a person of ordinary skill in the art will understand that the central operation processor may include other types of hardware.

The above-described apparatus may be implemented by using a hardware component, a software component, and/or a combination of a hardware component and a software component. For example, the apparatus and the component described in the exemplary embodiments may be implemented by using one or more general-purpose computers or a special-purpose computers such as, for example, a processor, a controller, an arithmetic logic unit (ALU), a digital signal processor, a microcomputer, a field programmable array (FPA), a programmable logic unit (PLU), a microprocessor, or any device that may execute an instruction and respond thereto.

A processor may execute an operating system (OS) and one or more software applications executed on the OS. Also, the processor may access, store, manipulate, process, and generate data in response to execution of software.

For convenience of understanding, though description has been made to the case where one processor is used, a person of ordinary skill in the art will understand that the processor may include a plurality of processing elements and/or processing elements having a plurality of types. For example, the processor may include a plurality of processors, or one processor and one controller. Also, the processor may include a different processing configuration such as a parallel processor.

Software may include a computer program, a code, an instruction, or a combination of one or more of these, and configure the processor to operate as desired, or instruct the processor independently or collectively.

Software and/or data may be embodied permanently or temporarily in a certain type of a machine, a component, a physical device, virtual equipment, a computer storage medium or device, or a transmitted signal wave in order to allow the processor to analyze the software and/or data, or to provide an instruction or data to the processor. Software may be distributed on a computer system connected via a network, and stored and executed in a distributed fashion. Software and data may be stored in one or more non-transitory computer-readable recording media.

The methods according to exemplary embodiments may be embodied in the form of program commands executable through various computer means, which may be recorded on a non-transitory computer-readable recording medium. The non-transitory computer-readable recording medium may include program commands, data files, and data structures either alone or in combination. The program commands recorded on the non-transitory computer-readable recording medium may be those that are especially designed and configured for the inventive concept, or may be those that are known and available to computer programmers skilled in the art.

Examples of the non-transitory computer-readable recording medium include magnetic recording media such as hard disks, floppy disks, and magnetic tapes, optical recording media such as CD-ROMs and DVDs, magneto-optical recording media such as floptical disks, and hardware devices such as ROMs, RAMs, and flash memories that are especially configured to store and execute program commands.

Examples of the program commands include machine language codes that may be generated by a compiler, and high-level language codes that may be executed by a computer by using an interpreter.

The above hardware device may be configured to operate as one or more software modules in order to perform an operation of an exemplary embodiment, and vice versa.

Though the exemplary embodiments have been described by a limited number of exemplary embodiments and drawings, a person of ordinary skill in the art will make various modifications and changes from the above exemplary embodiments. For example, even when the described technologies are performed in an order different from the described method and/or components such as the described system, structure, apparatus, and circuit are coupled or combined in a form different from the described method, or replaced by other components or equivalents thereof, a proper result may be accomplished.

Therefore, the scope of the inventive concept should not be limited and determined by the described exemplary embodiments, but should be determined by not only the following claims but also equivalents thereof.

What is claimed is:

1. A beamformer for performing analog beamforming of ultrasound signals received from a plurality of transducer devices, the beamformer comprising:
   first analog devices, comprising a first sample and hold circuit including sample capacitors controlled by a shift register, configured to output first ultrasound signals by delaying or transmitting the ultrasound signals based on a predetermined delay time;
   second analog devices, comprising a second sample and hold circuit, configured to output at least one ultrasound signal which is repeatedly used among the first ultrasound signals; and
   a processor configured to control the delay time, and to perform the analog beamforming by summing the first ultrasound signals, which correspond to the plurality of transducer devices and which are outputted depending on the delay time,
   wherein the first sample and hold circuit further comprises an output terminal for communication between the first sample and hold circuit and the second sample and hold circuit,
   wherein the second sample and hold circuit comprises:
      a capacitor, which is not controlled by the shift register, configured to store first sub-ultrasound signals when the first sub-ultrasound signals from among the first ultrasound signals are output from the first analog devices; and
      a control line configured to output the first sub-ultrasound signals stored in the capacitor when the first sub-ultrasound signals are repeatedly used in order to obtain an ultrasound image, the control line including at least two switches, and
   wherein the output terminal is selectively connected to the capacitor of the second sample and hold circuit by a control of the at least two switches.

2. The beamformer of claim 1, wherein the processor is further configured to obtain an ultrasound signal to be used at least two times by applying the clock signal to the control line.

3. The beamformer of claim 1, wherein the processor is further configured to control the first analog devices to transmit or receive each of the ultrasound signals depending on the delay time and output the first ultrasound signals.

4. The beamformer of claim 1, wherein the first sample and hold circuit in the first analog devices comprises:
   sample switches, one side of each of which are respectively connected to the plurality of transducer devices;
   sample capacitors respectively connected to the other sides of the sample switches;
   read-out switches one side of each of which are respectively connected to the sample capacitors, and the other sides are connected to the output terminal;
   the output terminal of the first ultrasound signals output from the read-out switches; and
   a switch controller configured to control a switching operation of the sample switches and the read-out switches.

5. The beamformer of claim 4, wherein the switch controller comprises:
   a first shift register configured to control the sample switches; and
   a second shift register configured to control the read-out switches.

6. The beamformer of claim 1, further comprising:
   a clock generator configured to generate a plurality of clock signals having different frequencies,
   wherein the first analog devices transmit or delay each of the received ultrasound signals by the delay time based on the plurality of clock signals.

7. The beamformer of claim 1, wherein when the plurality of transducer devices complete sampling of ultrasound signals received from a relevant focusing point, the processor is further configured to sum the first ultrasound signals which correspond to the plurality of transducer devices and which are outputted depending on the delay time by using an analog method.

8. The beamformer of claim 1, wherein the plurality of transducer devices are arranged in a one-dimensional (1D) manner or a two-dimensional (2D) manner.

9. An ultrasound imaging apparatus comprising:
   a two-dimensional (2D) transducer array comprising a plurality of transducer devices arranged in a horizontal direction and a vertical direction; and
   an analog beamformer configured to perform analog beamforming based on ultrasound signals received from the plurality of transducer devices,
   wherein the analog beamformer comprises:
      first analog devices, comprising a first sample and hold circuit including sample capacitors controlled by a shift register, configured to output first ultrasound signals by delaying or transmitting the ultrasound signals based on a predetermined delay time;
      second analog devices, comprising a second sample and hold circuit, configured to output at least one ultrasound signal which is repeatedly used among the first ultrasound signals; and
      a processor configured to control the delay time and to perform the analog beamforming by summing the first ultrasound signals, which correspond to the plurality of transducer devices and which are outputted depending on the delay time,
   wherein the first sample and hold circuit further comprises an output terminal for communication between the first sample and hold circuit and the second sample and hold circuit,
   wherein the second sample and hold circuit comprises:
      a capacitor, which is not controlled by the shift register, configured to store first sub-ultrasound signals when the first sub-ultrasound signals from among the first ultrasound signals are output from the first analog devices; and
      a control line configured to output the first sub-ultrasound signals stored in the capacitor when the first sub-ultrasound signals are repeatedly used in order to obtain an ultrasound image, the control line including at least two switches, and
   wherein the output terminal is selectively connected to the capacitor of the second sample and hold circuit by a control of the at least two switches.

10. The apparatus of claim 9, further comprising:
   a digital beamformer,
   wherein the analog beamformer performs beamforming inside a sub-aperture that divides the transducer devices by a predetermined number, and the digital beamformer performs beamforming between sub-apertures.

11. A method of performing analog beamforming of ultrasound signals received from a plurality of transducer devices in a beamformer comprising first analog devices, second analog devices, and a processor, the method comprising:

outputting, by the first analog devices comprising a first sample and hold circuit including sample capacitors controlled by a shift register, first ultrasound signals by delaying or transmitting the ultrasound signals based on a predetermined delay time;

storing, by the second analog devices comprising a second sample and hold circuit including a capacitor not controlled by the shift register, first sub-ultrasound signals in the capacitor when the first sub-ultrasound signals from among the first ultrasound signals are output from the first analog devices, and outputting, by a control line in the second sample and hold circuit, the first sub-ultrasound signals stored in the capacitor when the first sub-ultrasound signals are repeatedly used in order to obtain an ultrasound image, the control line including at least two switches; and performing, by the processor, the analog beamforming by summing the first ultrasound signals, which correspond to the plurality of transducer devices and which are outputted depending on the delay time, and the repeatedly used first sub-ultrasound signals, wherein the first sample and hold circuit further comprises an output terminal for communication between the first sample and hold circuit and the second sample and hold circuit, and wherein the outputting the first sub-ultrasound signals comprises selectively connecting the output terminal to the capacitor of the second sample and hold circuit by a control of the at least two switches.

12. The method of claim 11, further comprising:

controlling, by the processor, first analog devices to transmit or receive each of the ultrasound signals depending on the delay time and output the first ultrasound signals.

13. The method of claim 11, further comprising:

generating, by a clock generator in the beamformer, a plurality of clock signals having different frequencies, wherein the outputting of the first ultrasound signals comprises:

transmitting or delaying, by the first analog devices, each of the received ultrasound signals by the delay time based on the plurality of clock signals.

14. The method of claim 11, wherein the performing of the analog beamforming comprises:

completing, at the plurality of transducer devices, sampling of ultrasound signals received from a relevant focusing point.

15. The method of claim 11, wherein the plurality of transducer devices are arranged in a one-dimensional (1D) manner or a 2D manner.

16. The method of claim 11, further comprising:

performing analog beamforming inside a sub-aperture that divides the transducer devices by a predetermined number, and performing digital beamforming between sub-apertures.

17. A non-transitory computer-readable recording medium having recorded thereon a program for executing, a method of performing analog beamforming of ultrasound signals received from a plurality of transducer devices in a beamformer comprising first analog devices, second analog devices, and a processor, the method comprising:

outputting, by the first analog devices comprising a first sample and hold circuit including sample capacitors controlled by a shift register, first ultrasound signals by delaying or transmitting the ultrasound signals based on a predetermined delay time;

storing, by the second analog devices comprising a second sample and hold circuit including a capacitor not controlled by the shift register, first sub-ultrasound signals in the capacitor when the first sub-ultrasound signals from among the first ultrasound signals are output from the first analog devices, and outputting, by a control line in the second sample and hold circuit, the first sub-ultrasound signals stored in the capacitor when the first sub-ultrasound signals are repeatedly used in order to obtain an ultrasound image, the control line including at least two switches; and performing the analog beamforming by summing the first ultrasound signals, which correspond to the plurality of transducer devices and which are outputted depending on the delay time, and the repeatedly used first sub-ultrasound signals, wherein the first sample and hold circuit further comprises an output terminal for communication between the first sample and hold circuit and the second sample and hold circuit, and wherein the outputting the first sub-ultrasound signals comprises selectively connecting the output terminal to the capacitor of the second sample and hold circuit by a control of the at least two switches.

* * * * *